United States Patent
Glock

Patent Number: 5,116,339
Date of Patent: May 26, 1992

[54] ACETABULAR CUP INSTALLATION TOOL AND METHOD OF INSTALLING AN ACETABULAR CUP

[76] Inventor: Steven R. Glock, 5419 Damask Dr., Fort Wayne, Ind. 46815

[21] Appl. No.: 551,614

[22] Filed: Jul. 11, 1990

[51] Int. Cl.⁵ .............................................. A61B 17/56
[52] U.S. Cl. ......................................... 606/91; 606/81
[58] Field of Search ..................... 623/22; 606/91, 99, 606/104, 81

[56] References Cited

U.S. PATENT DOCUMENTS

| | | | |
|---|---|---|---|
| 3,859,992 | 1/1975 | Amstutz | 128/92 E |
| 4,224,698 | 9/1980 | Hopson | 3/1.912 |
| 4,263,903 | 4/1981 | Griggs | 128/92 B |
| 4,305,394 | 12/1981 | Bertuch, Jr. | 128/303 |
| 4,475,549 | 10/1984 | Oh | 128/303 R |
| 4,662,891 | 5/1987 | Noiles | 623/22 |
| 4,677,972 | 7/1987 | Tornier | 128/92 V |
| 4,716,894 | 1/1988 | Lazzeri et al. | 128/92 |
| 4,878,918 | 11/1989 | Tari et al. | 606/91 X |
| 4,994,064 | 2/1991 | Aboczky | 606/91 |

Primary Examiner—Robert A. Hafer
Assistant Examiner—Kevin G. Rooney
Attorney, Agent, or Firm—Baker & Daniels

[57] ABSTRACT

An installation tool has a head for engaging an acetabular cup, and an elongated member mounting the head adjacent an end that projects from the head and is insertable into an opening through the cup. The member end is expandable for engaging the cup at the opening to prevent movement of the cup relative to the member end and hold the cup in engagement with the head in order to move the cup with movement of the member end to place the cup for implanting at a desired position. The member end also is contractable for releasing the cup after implanting at the desired position. The elongated member is composed of a tubular shaft having a passage therethrough and a rod slidably disposed through the shaft passage. The member end is composed of a split collet with expandable and contractable jaws on one end of the shaft and an outwardly flared cam element formed on one end of the rod and extending between the collet jaws. A knob is mounted on the shaft and threadably fitted on the rod such that manual rotation of the knob in one or the other opposite directions will cause sliding movement of the rod relative to the shaft and of the cam element relative to the collet jaws to correspondingly expand or contract the jaws into or out of engagement with the cup at the central opening thereof.

20 Claims, 2 Drawing Sheets

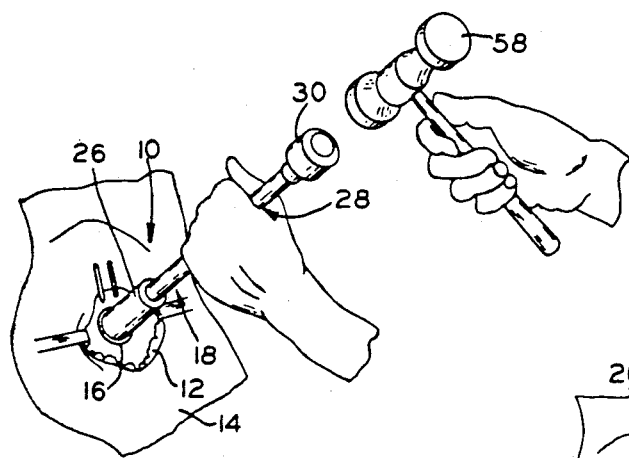
FIG_6
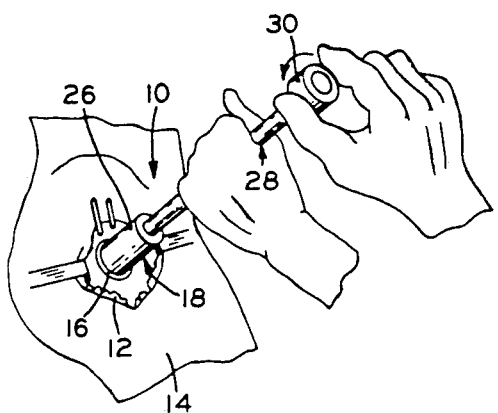
FIG_7
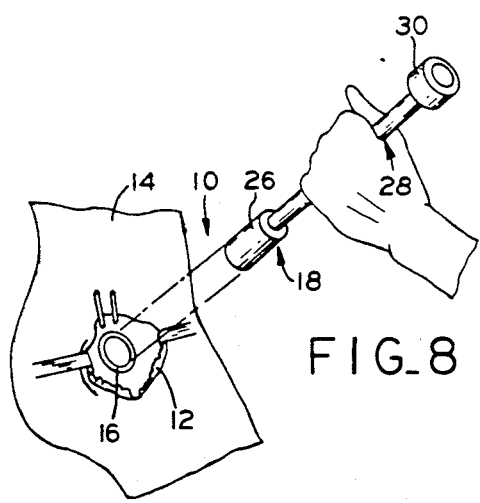
FIG_8
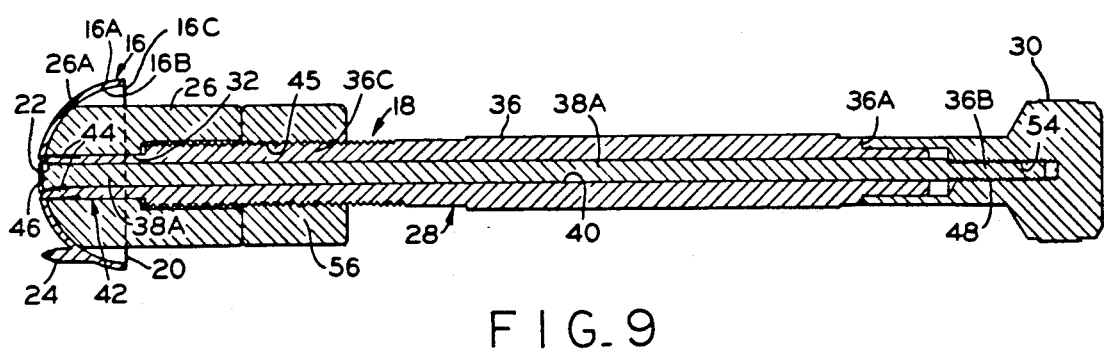
FIG_9

ACETABULAR CUP INSTALLATION TOOL AND METHOD OF INSTALLING AN ACETABULAR CUP

BACKGROUND OF THE INVENTION

The present invention relates generally to surgical instruments and, more particularly, to an acetabular cup installation tool and a method of installing the acetabular cup using the tool.

Total hip replacement is a surgical reconstructive procedure frequently performed by an orthopedic surgeon. It involves replacement of the acetabulum socket in the pelvis of the patient with an acetabular cup and replacement of the femoral neck on the femur of the patient with a prosthesis that has a ball adapted to engage in the acetabular cup.

In the procedure, the acetabulum socket is reamed out by the surgeon to enlarge it to receive the acetabular cup. The cup in effect will constitute a new socket and lining for the patient's acetabulum. The cup is then inserted in the reamed out recess and maneuvered to the proper angular orientation. Insertion and placement of the cup by the surgeon is carried out either by hand or by use of a hand tool that grips the cup.

The reamed out acetabulum which receives the cup is relatively inaccessible and thus it is difficult for the surgeon to see to maneuver the cup by hand into the proper position after insertion so that the cup can be screwed into place. Insertion and placement of the cup by use of a hand tool is preferred over placement by hand. However, most prior art placement tools are complicated, awkward and difficult to use.

One type of prior art positioning device engages the acetabular cup on the outer periphery thereof. A disadvantage to this type of device is that it obscures the vision of the surgeon in placing the cup, and the fact that it engages the cup on the outer periphery may interfere with full insertion of the cup into the socket. Another type of prior art positioner utilizes a vacuum to hold the cup as it is positioned. However, it is difficult to apply sufficient vacuum to securely hold the cup during positioning. Yet a further prior art device utilizes a screw connection between the positioner tool and the cup, but this limits the direction that the cup can be rotated during insertion and complicates the disengagement of the cup after it has been precisely positioned into the desired location in the socket.

Consequently, a need still exists for improvements in a hand tool and method for installing a acetabular cup for hip socket replacement.

SUMMARY OF THE INVENTION

The present invention provides an acetabular cup installation tool and socket replacement system and a method of installing the acetabular cup designed to satisfy the aforementioned needs. Improvements provided by the tool and system of the present invention enhance the ability of the surgeon to quickly and easily maneuver an inserted acetabular cup so as to place it in the exact position desired, to impact the acetabular cup with sufficient force to seat it at the exact position in which it was placed and to release acetabular cup without disturbing its placement and seated position.

Heretofore, just to achieve positioning and seating of the acetabular cup could take up to twenty-three minutes of a total procedure taking forty-five minutes. Now, by using the acetabular cup installation tool and method and acetabulum socket replacement system of the present invention it can ordinarily take under five minutes, or approximately one-fifth the previous amount of time, to position and seat the acetabular cup.

Accordingly, the present invention is directed to an acetabular cup installation tool which comprises: (a) a resilient body for receiving and positively engaging an acetabular cup at an interior surface of the cup; and (b) an elongated member mounting the body adjacent an end of the member with the end projecting from the body and insertable into an opening of the cup. The end of the member is expandable for engaging the cup at the opening to prevent movement of the cup relative to the member end and to hold the cup in engagement with the body in order to move the cup with movement of the member end to place the cup for implanting at a desired position. The end of the member is also contractable for releasing the cup after implanting at the desired position.

More particularly, in the preferred embodiment of the tool the elongated member includes an elongated tubular shaft having a longitudinal passage therethrough. The end of the member includes a split collet having expandable and contractable jaws defined on one end of the shaft. The resilient body is a head having an end surface for engaging the interior surface of the cup. The body also has a central bore therethrough receiving the shaft with at least respective tips of the collet jaws projecting from the bore of the head and into the opening of the cup when the cup is engaged with the head end surface.

Also, the elongated member includes an elongated rod disposed through the passage of the shaft for longitudinal sliding movement relative thereto. The end of the member also includes an outwardly flared cam element formed on one end of the rod and extending between and disposable beyond the collet jaws. The rod has external threads on the other end. The tool also comprises a knob movably mounted on the other end of the shaft. The knob has internal threads complementary to and interfitted with the external threads on the other end of the rod. Manual rotation of the knob in one or the other opposite directions causes longitudinal sliding movement of the rod relative to the shaft and of the flared cam element relative to the collet jaws to correspondingly expand or contract the jaw tips into or out of engagement with the cup at the opening thereof.

Also, the present invention relates to a system for replacement of an acetabulum socket which comprises an acetabular cup having a central opening and an elongated tool as defined above having an end actuatable between expanded and contracted conditions for engaging and releasing the cup. The tool end may be round or of a non-circular configuration complementary to the configuration of the cup opening for keying the tool end into the cup opening and, when engaged with the cup, for ensuring movement of the cup with movement of the tool end in order to place the cup for implanting at a desired position. If desired, the opening of the acetabular cup may have a hexagonal configuration.

Further, the present invention is directed to a method of installing an acetabular cup in a pelvic socket. The method comprises the steps of: (a) placing a forward end of a tool being actuatable between contracted and expanded conditions through a central opening in an acetabular cup; (b) actuating the tool forward end from the contracted to expanded condition to engage and grip the cup at its central opening to prevent movement of the cup relative to the tool end and to hold the cup in engagement against the forward end surface of a holder head of the tool; and (c) maneuvering the tool to move the tool end and the cup retained thereon to place the cup for implanting at the desired position in a pelvis socket. Further, the method comprises the step of seating the cup in the desired position in the socket in which it was previously placed by striking against a rearward end of the tool. Further, the method comprises the step of actuating the tool forward end from the expanded to contracted condition to disengage and release the grip on the cup to enable withdrawing of the tool from the cup after seating and implanting of the cup in the socket.

By engaging the cup on an inner surface thereof, the surgeon's vision is not obscured and he is able to accurately maneuver the cup into position in the socket. Furthermore, unlike the vacuum holders used previously, the holding tool according to the present invention positively engages two surfaces on the interior of the cup by a clamping action so that the cup is securely held on the end of the tool and cannot be pulled off even with the application of considerable force.

A further advantage to the invention, in a preferred form thereof, is the ability to utilize the tool as an impacting device to fully seat the cup after it has been positioned. To avoid damage to the soft tissue underneath the cup, the gripping portion of the tool can be retracted inside the head.

These and other features and advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 6 is a schematic perspective view of the tool being used, illustrating impacting of the tool by a mallet head to seat and thereby implant the cup at the exact desired position in which it was previously placed by manual maneuvering of the tool.

FIG. 7 is another schematic perspective view of the tool being used, illustrating adjusting of the tool to release its cup-engaging end from the cup after seating and thus after implanting of the cup has been achieved at the desired position.

FIG. 8 is a still another schematic perspective view of the tool, illustrating withdrawing of the tool from the implanted cup.

FIG. 9 is another longitudinal axial sectional view of the installation tool of the present invention similar to FIG. 1, but illustrating the cup-engaging end of the tool in a retracted position and contracted condition relative to an acetabular cup for withdrawing the tool from the cup.

DETAILED DESCRIPTION OF THE INVENTION

Figure 1:
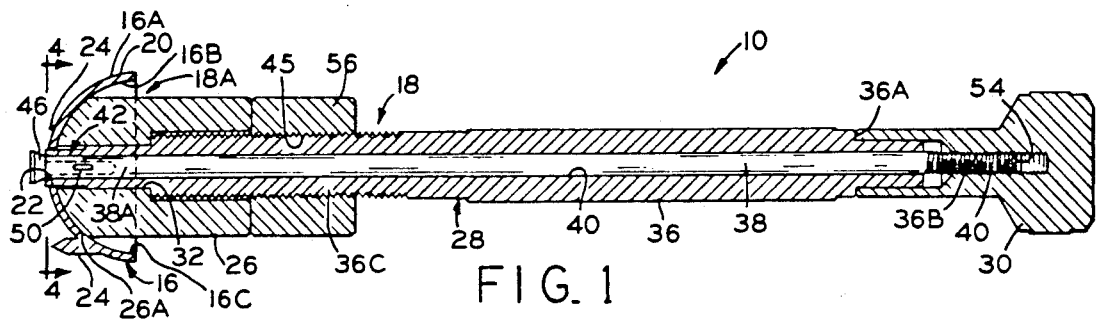
FIG. 1 is a longitudinal axial sectional view of an acetabular cup installation tool of the present invention illustrating a cup-engaging end of the tool in an extended position and in a contracted condition relative to an acetabular cup.
Figure 4:
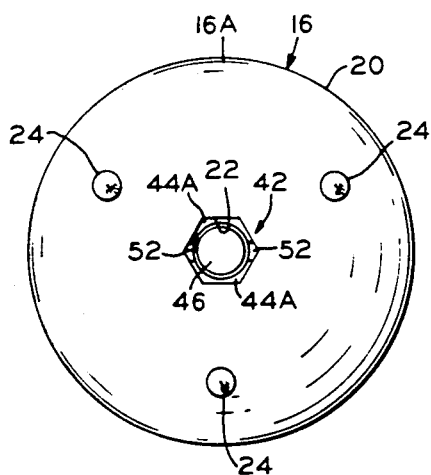
FIG. 4 is an enlarged end elevational view of the cup-engaging end of the tool and an exterior end view of the acetabular cup as seen along line 4—4 of FIG. 1.
Figure 5:
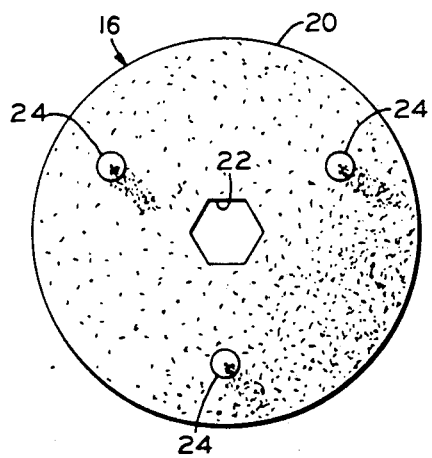
FIG. 5 is an enlarged exterior end elevational view of the acetabular cup of FIG. 1 by itself.

Referring now to the drawings, and particularly to FIGS. 1 and 9, there is illustrated a system 10 of the present invention for use in replacing and reconstructing an acetabulum socket 12 on the pelvis 14 of a patient, as depicted schematically in FIGS. 6-8. The socket replacement system 10 includes an acetabular cup 16 and an installation tool 18 of the present invention. The acetabular cup 16 is a curved metal plate 20 formed in a hemispherical shape defining a posterior opening 16C. As also seen in FIGS. 4 and 5, the cup 16 has an anterior opening 22 which may be of a circular or non-circular, preferably hexagonal, configuration defined at a central location through the plate 20. The cup 16 also has a plurality of spikes 24 fixed on and extending forwardly from an exterior surface 16A of the cup which facilitate retention of the cup 16 in the desired position once implanted in the pelvis 14 of the patient. The outer surface 16A may comprise a POROCOAT finish. Once the cup 16 is implanted, a hemispherical-shaped plastic liner (not shown) is inserted within the cup 16 into close fitting relationship with an interior surface 16B thereof.

Generally, the cup installation tool 18 of the system 10 is elongated and has a forward cup-engaging end 18A actuatable between expanded and contracted conditions for engaging and releasing the cup 16. The tool end 18A may also be of a non-circular cross-sectional configuration complementary to the non-circular configuration of the cup opening 22 for keying the tool end 18A into the cup opening 22. Cup openings are also possible. Therefore, when the tool end 18A is engaged with the cup 16, increments of movement of the cup 16 will precisely match the increments of movement of the tool 18, ensuring the surgeon using the tool 18 accurate control in maneuvering and placing the cup 16 for implanting at a desired position.

Preferably, the non-circular configurations of the cup opening 22 and tool end 18A are both hexagonal; however, other configurations, such as oblong and triangular, are possible, the requirement in a preferred embodiment being that the shape of the cup opening 22 not permit relative movement, particularly rotation, between the cup 16 and the end 18A of the tool 18 inserted through the opening 22. Circular openings are also possible. Therefore, the cup 16 can be precisely rotated by the surgeon manually maneuvering the tool 18 to rotate the tool end 18A in order to accurately place the cup 16 for implanting at the desired position in the pelvis socket 12 of the patient. It may also be possible to utilize a round opening in the cup 16, although this configuration is not preferred. The metal parts of the tool are preferably made of stainless steel. Although opening 22 preferably extends through cup 16, it may also be possible to form opening 22 as an inwardly opening recess in the cup having sidewalls which can be gripped by the tool.

Referring to FIGS. 1-3 and 9, in its basic components, the cup installation tool 18 includes a cup holder body 26, an elongated member 28 mounting the holder body 26, and a knob 30 mounted to the member 28. The holder body 26 of the installation tool 18 is in the form of a generally cylindrical head 26. The holder head 26 is composed of a suitable metal or plastic material, such as high impact Delrin, and has a forward curved end surface 26A, preferably of hemispherical shape, for receiving and engaging the cup 16 at its interior surface 16B having the hemispherical shape also. The holder head 26 also has a central bore 32 defined therethrough.

The elongated member 28 of the installation tool 18 is composed of an outer elongated hollow shaft 36 and an inner elongated cylindrical rod 38. The outer hollow shaft 36 has a longitudinal cylindrical passage 40 defined therethrough. The actuatable end 18A of the tool 18 includes a split collet 42 having expandable and contractable jaws 44 defined on a forward end of the tubular shaft 36. Also, the shaft 36 has an abutment surface 36A defined adjacent a rearward end 36B of the shaft 36. Further, the shaft 36 mounts the holder head 26 about its forward end with the collet jaws 44 extending through the bore 32 of the head 26. A forward portion 36C of the shaft 36 rearwardly of the collet 42 has external threads 45.

Figure 2:
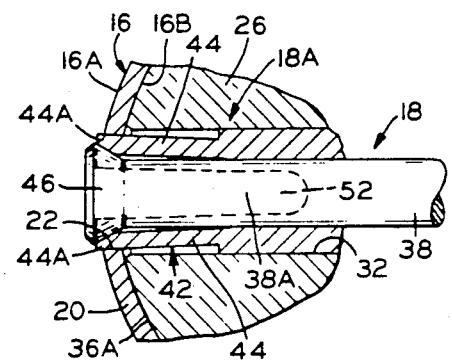
FIG. 2 is an enlarged fragmentary view of the cup-engaging end of the tool of FIG. 1, illustrating the tool end in the retracted position and in an expanded condition relative to the cup for engaging and holding the acetabular cup.
Figure 3:
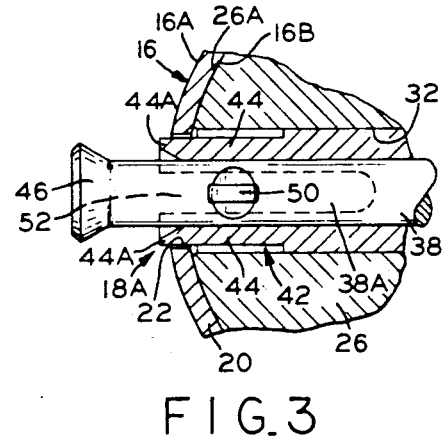
FIG. 3 is an enlarged fragmentary view similar to that of FIG. 2, but illustrating the tool end in the extended position and contracted condition of FIG. 1 for disengaging and releasing the acetabular cup.

At least the respective tips 44A of the collet jaws 44 project forwardly from the head bore 32 and insert into the central opening 22 of the cup 16, as seen in FIGS. 1-3. In the case of a non-circular opening, the respective jaw tips 44A are preferably trapezoidal in cross-section, as can be seen in FIG. 4, such that together the jaw tips 44A define an overall hexagonal configuration complementary to the hexagonal configuration of the cup central opening 22.

The collet jaws 44 normally assume a contracted condition, as seen in FIG. 3, in which they are disposed radially inwardly in spaced relation from the portion of the cup 16 defining the central opening 26 thereof and thus are disengaged and released from the cup 16. The jaws 44 are expandable or spreadable radially outwardly, as seen in FIGS. 1, 2 and 4, for engaging and gripping the cup 16 at the sidewalls of its central opening 22 to prevent movement of the cup 16 relative to the tool 18 and to hold the cup 16 in engagement against the forward end surface 26A holder head 26. So engaged on and held against the forward end surface 26A of the head 26, the acetabular cup 16 will remain stationary on the head 26 and will move with the tool 18 as the tool is manipulated and rotated to place the cup for implanting at the desired position in the socket 12.

The elongated rod 38 of the tool member 36 is disposed through the passage 40 of the hollow shaft 36 and slidably movable axially or longitudinally relative to the shaft. The rod 38 has an outwardly flared cam element 46 formed on its forward end 38A and external threads 48 formed on its rearward end 38B. The forward end 38A of the rod 38 extends between the collet jaws 44. Forward longitudinal movement of the rod 38 relative to the shaft 36 disposes the cam element 46 beyond and spaced from the tips 44A of the collet jaws 44, permitting the jaws 44 to assume their normal retracted condition, as seen in FIG. 3. On the other hand, rearward longitudinal movement of the rod 38 relative to the shaft 36 brings the cam element 46 into engagement with the jaw tips 44A, forcing the jaws 44 to spread radially apart and assume their expanded condition, as seen in FIGS. 2 and 4. The opposite sides of the forward end 38A of the rod 38 have ears 50 formed thereon, such as by a conventional swaging operation, which are guided in the spaces or slots 52 present between the pair of collet jaws 44, as seen in FIGS. 2-4.

The knob 30 of the installation tool 18 is manipulated by turning it manually to cause selected longitudinal sliding movement of the rod 38 relative to the shaft 36 of the elongated tool member 28. The knob 30 is movably mounted on the rearward end 36B of the shaft 36 adjacent its abutment surface 36A. Also, the knob 30 has internal threads 54 complementary to and interfitted with the external threads 48 on the rearward end 38B of the rod 38. In view of the fact that the pair of ears 50 on opposite sides of the forward end 38A of the rod 38 prevents rotation of the rod 38 relative to the shaft 36, manual rotation of knob 30 in one or the other of clockwise or counterclockwise directions will cause the longitudinal sliding movement of the rod 38 in the desired direction relative to the shaft 36 and corresponding actuation (expansion or contraction) of the collet jaw tips 44A by the flared cam element 46 into or out of engagement with the cup 16 at its central opening 22. In the preferred form of the invention described above, jaws 44 preferably expand outwardly against sidewalls of opening 22, but an alternative construction (not shown) wherein the jaws would grip inwardly against a protrusion or the like on the inner surface of the cup 16 is also possible. However, such an alternative configuration is not preferred.

The installation tool 18 also includes a stop collar 56 threadably mounted by the external threads 45 on the forward portion 36C of the shaft 36. The stop collar 56 retains the head 26 in the desired position on the shaft 36 during the aforementioned placement of the cup in the desired position for implanting in the socket 12.

In FIGS. 1-3, the jaw tips 44A of the split collet 42 on the cup-engaging end 18A of the tool 18 are shown disposed in an extended position in which they project through the central opening 22 and forwardly of the exterior surface 16A of the cup 16. In such extended position, the jaw tips 44A can be actuated from contracted to expanded condition for engaging the acetabular cup 16. On the other hand, in FIG. 9, the jaw tips 44A of the split collet 42 on the cup-engaging end 18A of the tool 18 are shown disposed in a retracted position in which they are now withdrawn rearwardly of the exterior surface 16A of the cup 16. The collet 42 in the retracted position is now disposed relative to the cup 16 in preparation for implanting the cup 16 in the socket 12. In the retracted position, the collet 42 cannot contact the bone material defining the socket 12 and thus will not be damaged by the implanting of the cup into the socket.

In order move the collet 42 to the retracted position, the shaft 36 must be moved rearwardly relative to the holder head 26 mounted about the shaft. This is accomplished by rotating the lock collar 56 in a direction which advances it further toward the holder head 26. Such rotation instead causes withdrawal of the collet jaw tips 44A rearwardly such that they no longer project forwardly of the exterior surface 16A of the cup 16. Once the collet jaw tips 44A have been retracted, then the procedures for implanting the cup 16 can be performed.

FIGS. 6-8 depict the procedures for partially implanting the cup 16 using the installation tool 18 and for afterwards removing the tool 18 from the implanted cup. FIG. 6 illustrates impacting the knob 30 of the tool 18 by a mallet head 58 to seat and thereby seat the cup 16 at the exact desired position in which it was previously placed by manually maneuvering of the tool 18. In view that the knob 30 engages the rear abutment surface 36A on the tool shaft 36, hitting the knob 30 will not cause damage to its internal threads 54 nor to the external threads 48 on the rod 38. FIG. 7 illustrates adjusting the tool 18 to release its cup-engaging end 18A from the cup 16 after the seating. The knob 30 on the tool 18 can be impacted again to fully implant the cup at the desired position. Finally, FIG. 8 illustrates the withdrawal of the tool 18 from the cup 16 now implanted in the socket 12.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the forms hereinbefore described being merely preferred or exemplary embodiments thereof.

What is claimed is:

1. A tool for installing an acetabular cup having an anterior opening and a posterior opening, said tool comprising:
   a cup holder body adapted for extending through the posterior opening of the cup and for engaging the acetabular cup at an interior surface of the cup; and
   an elongated member mounting said cup holder body adjacent an end of said member with said end projecting from said cup holder body and being insertable into the anterior opening formed at the interior surface of and extending at least partially through said cup, said end of said elongated member being expandable for engaging the cup at the anterior opening to prevent movement of the cup relative to said elongated member end and hold the cup in engagement against the cup holder body in order to move the cup with movement of said elongated member and thereby place the cup for implanting at a desired position, said end of said elongated member being contractable for releasing the cup after implanting at the desired position.

2. An acetabular cup installation tool, comprising:
   a holder body for receiving and engaging an acetabular cup at an interior surface of the cup; and
   an elongated member mounting said body adjacent an end of said member with said end projecting from said body and insertable into an opening of the cup, said end of said member being expandable for engaging the cup at the opening to prevent movement of the cup relative to said member end and hold the cup in engagement against the body in order to move the cup with movement of said member end to place the cup for implanting at a desired position, said end of said member being contractable for releasing the cup after implanting at the desired position;
   said elongated member including an elongated tubular shaft having a longitudinal passage therethrough; and
   said end of said member having a split collet defined on one end of said shaft.

3. The tool of claim 2, wherein said shaft has an abutment surface defined adjacent the other end thereof.

4. The tool of claim 2, wherein said split collet includes expandable and contractable jaws formed on said one end of said shaft.

5. The tool of claim 4, wherein said holder body is a head having a curved end surface for engaging the interior surface of the cup and a central bore therethrough receiving said shaft with at least respective tips of said collet jaws projecting from said bore of said head and into the interior opening of the cup when the cup is engaged against said head end surface.

6. The tool of claim 4, wherein said elongated member further includes an elongated rod disposed through said passage of said shaft for longitudinal sliding movement relative thereto, said rod having an outwardly flared cam element formed on one end and extending between and disposable beyond said collet jaw tips, said rod having external threads on the other end.

7. The tool of claim 6, further comprising:
   a knob movably mounted on said other end of said shaft and having internal threads complementary to and interfitted with said external threads on said other end of said rod such that manual rotation of said knob in one or the other opposite directions causes longitudinal sliding movement of said rod relative to said shaft and of said cam element relative to said collet jaws to correspondingly expand or contract said jaw tips into or out of engagement with the cup at the opening thereof.

8. An acetabular cup installation tool, comprising:
   an elongated tubular shaft having a longitudinal passage therethrough and including a split collet defining expandable and contractable jaws on one end of said shaft, and an abutment surface defined adjacent the other end of said shaft;
   a holder body having a curved end surface for engaging an interior surface of an acetabulum cup and a central bore therethrough receiving said shaft with at least respective tips of said collet jaws projecting from said bore of said body and insertable into a central opening and beyond an exterior surface of the cup when the cup is engaged against said body end surface;
   an elongated rod disposed through said passage of said shaft for longitudinal sliding movement relative thereto and including an outwardly flared cam element formed on one end of said rod and extending between and disposable beyond said collet jaw tips, said rod having external threads on the other end; and
   a knob movable mounted on the other end of the shaft adjacent and in engagement with said abutment surface thereof and having internal threads complementary to and interfitted with said external threads on said other end of said rod such that manual rotation of said knob in one or the other opposite directions causes longitudinal sliding movement of said rod relative to said shaft and of said cam element relative to said collet jaws to correspondingly expand or contract said jaw tips into or out of engagement with the cup at the central opening thereof.

9. The tool of claim 8, further comprising:
   a collar rotatably mounted on said shaft rearwardly of said holder head and adjustable relative to said shaft and head for causing retraction of said shaft relative to said head to withdraw said collet jaw tips from projecting beyond the exterior surface of the cup.

10. A system for replacement of an acetabulum socket, comprising:

an acetabular cup having a posterior opening and an anterior opening formed at the interior surface of and extending at least partially through said cup; and an elongated tool that extends through the posterior opening of the cup and having an end actuatable between expanded and contracted conditions for frictionally engaging said anterior cup opening when expanded and releasing said cup when contracted, and, when said tool end is engaged with said cup, for ensuring movement of said cup with movement of said tool end in order to place said cup for implanting at a desired position.

11. The system of claim 10, wherein said opening of said cup has a non-circular configuration.

12. The system of claim 10 wherein said tool end comprises a split collet having expandable and contractable jaws.

13. A system for replacement of an acetabulum socket, comprising:

an acetabular cup having a central opening; and an elongated tool having an end actuatable between expanded and contracted conditions for frictionally engaging said opening when expanded and releasing said cup when contracted, and, when said tool end is engaged with said cup, for ensuring movement of said cup with movement of said tool end in order to place said cup for implanting at a desired position; and a tubular shaft having a longitudinal passage therethrough, said end of said tool including a split collet defined on one end of said shaft.

14. The system of claim 13, wherein said shaft has an abutment surface defined adjacent the other end thereof.

15. The system of claim 13, wherein said split collet includes expandable and contractable jaws formed on said one end of said shaft.

16. The system of claim 15, wherein said tool also includes a holder body having a curved end surface for engaging said interior surface of said cup and a central bore therethrough receiving said shaft with at least respective tips of said collet jaws projecting from said bore of said body and into the opening of the cup when the cup is engaged with said body end surface.

17. The system of claim 16, wherein said tool further includes a rod disposed through said passage of said shaft for longitudinal sliding movement relative thereto, said rod having an outwardly flared cam element formed on one end and extending between and disposable beyond said collet jaw tips, said rod also having external threads on the other end.

18. The system of claim 17, wherein said tool further includes a knob rotatably mounted on said other end of said shaft and having internal threads complementary to and interfitted with said external threads on said other end of said rod such that manual rotation of said knob in one or the other opposite directions causes longitudinal sliding movement of said rod relative to said shaft and of said cam element relative to said collet jaws to correspondingly expand or contract said jaw tips into or out of engagement with the cup at the opening thereof.

19. A method of installing an acetabular cup having an anterior opening and a posterior opening therein, comprising the steps of:

inserting the forward end of a tool through the posterior cup opening, placing the forward end of a tool into the anterior opening formed at the interior surface of and extending at least partially through the acetabular cup;

expanding the tool forward end to engage and grip the cup at said anterior opening to prevent movement of the cup relative to the tool end and to hold the cup in engagement against the forward end surface of a cup holder body of the tool;

maneuvering the tool to move the tool end and the cup retained thereon to place the cup for implanting at the desired position in a pelvis socket; and contracting the tool forward end to disengage and release the grip on the cup to enable withdrawing of the tool from the cup after seating and implanting of the cup in the socket.

20. The method of claim 19, further comprising:

seating the cup in the desired position in the socket in which it was previously placed by pounding against a rearward end of the tool.

* * * * *